(12) United States Patent
Ferrera et al.

(10) Patent No.: US 6,872,218 B2
(45) Date of Patent: Mar. 29, 2005

(54) VARIABLE STIFFNESS COIL FOR VASOOCCLUSIVE DEVICES

(75) Inventors: David A. Ferrera, San Francisco, CA (US); Daniel R. Kurz, Sunnyvale, CA (US)

(73) Assignee: Micrus Corporation, Mountain View, CA (US)

( * ) Notice: Subject to any disclaimer, the term of this patent is extended or adjusted under 35 U.S.C. 154(b) by 6 days.

(21) Appl. No.: 10/705,517

(22) Filed: Nov. 10, 2003

(65) Prior Publication Data

US 2004/0106946 A1 Jun. 3, 2004

Related U.S. Application Data

(60) Continuation of application No. 09/991,021, filed on Nov. 15, 2001, now Pat. No. 6,656,201, which is a division of application No. 09/211,783, filed on Dec. 15, 1998, now Pat. No. 6,383,204.

(51) Int. Cl.$^7$ .............................................. A61M 29/00
(52) U.S. Cl. ...................................... 606/200; 606/191
(58) Field of Search ................................ 606/191, 200

(56) References Cited

U.S. PATENT DOCUMENTS

| | | | |
|---|---|---|---|
| 1,341,052 A | | 5/1920 | Gale |
| 1,667,730 A | | 5/1928 | Green |
| 2,078,182 A | | 4/1937 | MacFarland |
| 2,549,335 A | | 4/1951 | Rahthus |
| 3,334,629 A | | 8/1967 | Cohn |
| 3,452,742 A | | 7/1969 | Muller |
| 3,649,224 A | | 3/1972 | Anderson et al. |
| 3,868,956 A | | 3/1975 | Alfidi et al. |
| 4,494,531 A | | 1/1985 | Gianturco |
| 4,503,569 A | * | 3/1985 | Dotter ........................ 128/325 |
| 4,512,338 A | | 4/1985 | Balko et al. |
| 4,553,545 A | | 11/1985 | Maass et al. |

(Continued)

FOREIGN PATENT DOCUMENTS

| | | |
|---|---|---|
| DE | 32 03 410 A1 | 11/1982 |
| DE | 197 04 269 A1 | 11/1997 |
| EP | 0 183372 A1 | 6/1986 |
| EP | 0 382014 A1 | 8/1990 |
| EP | 0 747 012 A1 | 11/1996 |
| EP | 0 747 014 A1 | 11/1996 |
| EP | 0 820 726 A2 | 1/1998 |
| GB | 2 066 839 A | 7/1981 |
| WO | WO 94/10936 | 5/1994 |
| WO | WO 94/16629 | 8/1994 |
| WO | WO 95/18585 | 7/1995 |
| WO | WO 97/48351 | 12/1997 |
| WO | WO 99/07294 | 2/1999 |
| WO | WO 99/29260 | 6/1999 |

OTHER PUBLICATIONS

"Dictionary of Metallurgy" by Birchon, p. 182, 1965.*

Tottle, C.R., "An Encyclopaedia of Metallurgy and Materials", pp. 3, 11, 323–4, 1985.*

Y. Pierre Gobin, M.D., et al., "Treatment of Large and Giant Fusiform Intracranial Aneurysms with Guglielmi Detachable Coils," J. Neurosurg., Jan. 1996, pp. 55–62, vol. 84.

(Continued)

*Primary Examiner*—Gary Jackson
(74) *Attorney, Agent, or Firm*—Fulwider Patton Lee & Utecht, LLP

(57) ABSTRACT

The variable stiffness vasoocclusive coil is given variable stiffness along the length of the coil by selectively heat treating certain segments of a primary or secondary coil. The primary coil can be selectively heat treated to form soft or deformable segments along the length of the coil, and can then be shaped into a secondary shape that is set by a heat treatment process. Distal regions of the coil can also be heat treated to make the distal ends of the coil softer, more deformable, or less traumatic.

3 Claims, 2 Drawing Sheets

U.S. PATENT DOCUMENTS

| | | |
|---|---|---|
| 4,638,803 A | 1/1987 | Rand |
| 4,655,771 A | 4/1987 | Wallsten |
| 4,695,426 A | 9/1987 | Nylund |
| 4,718,907 A | 1/1988 | Karwoski et al. |
| 4,748,986 A | 6/1988 | Morrison et al. |
| 4,768,507 A | 9/1988 | Fischell et al. |
| 4,795,458 A | 1/1989 | Regan |
| 4,800,882 A | 1/1989 | Gianturco |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,950,258 A | 8/1990 | Kawai et al. |
| 4,954,126 A | 9/1990 | Wallsten |
| 4,957,479 A | 9/1990 | Roemer |
| 4,957,501 A | 9/1990 | Lahille et al. |
| 4,990,155 A | 2/1991 | Wilkoff |
| 4,994,069 A | 2/1991 | Ritchart et al. |
| 5,026,377 A | 6/1991 | Burton et al. |
| 5,041,084 A | 8/1991 | DeVries et al. |
| 5,064,435 A | 11/1991 | Porter |
| 5,071,407 A | 12/1991 | Termin et al. |
| 5,104,404 A | 4/1992 | Wolff |
| 5,108,407 A | 4/1992 | Geremia et al. |
| 5,122,136 A | 6/1992 | Guglielmi et al. |
| 5,133,731 A | 7/1992 | Butler et al. |
| 5,133,732 A | 7/1992 | Wiktor |
| 5,139,243 A | 8/1992 | Balsells |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,160,341 A | 11/1992 | Brenneman et al. |
| 5,176,625 A | 1/1993 | Brisson |
| 5,176,661 A | 1/1993 | Evard et al. |
| 5,183,085 A | 2/1993 | Timmermans |
| 5,186,992 A | 2/1993 | Kite, III |
| 5,203,772 A | 4/1993 | Hammerslag et al. |
| 5,211,183 A | 5/1993 | Wilson |
| 5,217,484 A | 6/1993 | Marks |
| 5,222,969 A | 6/1993 | Gillis |
| 5,226,911 A | 7/1993 | Chee et al. |
| 5,228,453 A | 7/1993 | Sepetka |
| 5,234,437 A | 8/1993 | Sepetka |
| 5,234,456 A | 8/1993 | Silvestrini |
| 5,250,071 A | 10/1993 | Palermo |
| 5,256,146 A | 10/1993 | Ensminger et al. |
| 5,261,916 A | 11/1993 | Engelson |
| 5,269,752 A | 12/1993 | Bennett |
| 5,304,194 A | 4/1994 | Chee et al. |
| 5,304,195 A | 4/1994 | Twyford, Jr. et al. |
| 5,312,356 A | 5/1994 | Engelson et al. |
| 5,312,415 A | 5/1994 | Palermo |
| 5,334,210 A | 8/1994 | Gianturco |
| 5,336,205 A | 8/1994 | Zenzen et al. |
| 5,342,387 A | 8/1994 | Summers |
| 5,350,397 A | 9/1994 | Palermo et al. |
| 5,354,295 A | 10/1994 | Guglielmi et al. |
| 5,380,304 A | 1/1995 | Parker |
| 5,382,259 A | 1/1995 | Phelps et al. |
| 5,417,708 A | 5/1995 | Hall et al. |
| 5,421,338 A | 6/1995 | Crowley et al. |
| 5,437,282 A | 8/1995 | Koger et al. |
| 5,441,516 A | 8/1995 | Wang et al. |
| 5,443,478 A | 8/1995 | Purdy |
| 5,514,176 A | 5/1996 | Bosley, Jr. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,562,641 A | 10/1996 | Flomenblit et al. |
| 5,562,698 A | 10/1996 | Parker |
| 5,569,245 A | 10/1996 | Guglielmi et al. |
| 5,582,619 A | 12/1996 | Ken |
| 5,601,600 A | 2/1997 | Ton |
| 5,607,445 A | 3/1997 | Summers |
| 5,624,449 A | 4/1997 | Pham et al. |
| 5,624,461 A * | 4/1997 | Mariant ............... 606/191 |
| 5,637,113 A | 6/1997 | Tartaglia et al. |
| 5,639,277 A * | 6/1997 | Mariant et al. ........ 606/191 |
| 5,643,254 A | 7/1997 | Scheldrup et al. |
| 5,645,082 A | 7/1997 | Sung et al. |
| 5,645,558 A | 7/1997 | Horton |
| 5,649,949 A | 7/1997 | Wallace et al. |
| 5,667,522 A | 9/1997 | Flomenblit et al. |
| 5,669,905 A | 9/1997 | Scheldrup et al. |
| 5,669,931 A | 9/1997 | Kuplecki et al. |
| 5,676,697 A | 10/1997 | McDonald |
| 5,690,643 A | 11/1997 | Wijay |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,697,948 A | 12/1997 | Marin et al. |
| 5,700,258 A | 12/1997 | Mirigian et al. |
| 5,718,711 A | 2/1998 | Berenstein et al. |
| 5,725,546 A | 3/1998 | Samson |
| 5,733,329 A | 3/1998 | Wallace et al. |
| 5,743,905 A | 4/1998 | Eder et al. |
| 5,746,769 A | 5/1998 | Ton et al. |
| 5,749,891 A * | 5/1998 | Ken et al. ............ 606/200 |
| 5,749,894 A | 5/1998 | Engelson |
| 5,766,160 A | 6/1998 | Samson et al. |
| 5,800,453 A | 9/1998 | Gia |
| 5,800,455 A | 9/1998 | Palermo et al. |
| 5,800,520 A | 9/1998 | Fogarty et al. |
| 5,807,404 A | 9/1998 | Richter |
| 5,824,037 A | 10/1998 | Fogarty et al. |
| 5,830,230 A * | 11/1998 | Berryman et al. ...... 606/200 |
| 5,843,118 A | 12/1998 | Sepetka et al. |
| 5,944,733 A * | 8/1999 | Engelson ............ 606/191 |
| 6,013,084 A * | 1/2000 | Ken et al. ............ 606/108 |

OTHER PUBLICATIONS

Cameron G. McDougall, M.D., et al., "Endovascular Treatment of Basilar Tip Aneurysms using Electrolytically Detachable Coils," J. Neurosurg., Mar. 1996, pp. 393–399, vol. 84.

Sadek K. Hilal, M.D. et al., Journal of Neurological Surgery "Therapeutic Percutaneous Embolization for Extra-Axial Vascular Lesions of the Head, Neck and Spine" Sep., 1975; pp. 275–287.

Stephen L. Kaufman, M.D. et al., Investigative Radiology, May–Jun. 1978 "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar, Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975 "Selective Arterial Embolization for Control of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

Sidney Wallace, M.D. et al., Cancer, Oct. 1979 "Arterial Occlusion of Pelvic Bone Tumors"; pp. 322–325 & 661–663.

"Mechanical Devices for Arterial Occlusion" by C. Gianturco, M.D., et al., Jul. pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occulusion of Experimental Arteriovenous Fistulas", By James H. Anderson, et al., Am. J. Roentgenol, Nov. 1977, pp. 795–798.

"Mini' Gianturco Stainless Steel Coils for Transcatheter Vascular Occlusion" James H. Anderson, et al., From The Department of Diagnostic Radiology at the University of Texas System Cancer Center, Aug. 1978, pp. 301–303.

"A New Improved Coil for Tapered–Tip Catheter for Arterial Occlusion" By Vince P. Chuang, M.D., et al., May 1980, pp. 507–509.

"Neurosurgery Interactive Article Part 2—Clinical Studies Embolization of Cerebral Arteriovenous Malformations: Part II–Aspects of Complications and Late Outcome" by Christer Lunqvist, M.D. Ph.D., et al., Sep. 1996, pp. 1–16.

"Shape Memory Alloys" By Jeff Perkins, pp. 1095–1096.

Christos A. Athanasoulis, M.D. The New England Journal of Medicine, May 15, 1980 "Therapeutic Applications of Angiography" pp. 1117–1125 (1 of 2).

Christos A. Athanasoulis, M.D. The New England Journal of Medicine, May 22, 1980 "Therapeutic Applications of Angiography" pp. 1174–1179 (2 of 2).

Alex Berenstein, M.D. and Irvin I. Kricheff, M.D. "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part. II. Novel Microcrystals of Polymers" pp. 481–498.

* cited by examiner

VARIABLE STIFFNESS COIL FOR VASOOCCLUSIVE DEVICES

RELATED APPLICATIONS

This is a continuation of Ser. No. 09/991,021, filed Nov. 15, 2001 now U.S. Pat. No. 6,656,201 which is a divisional of Ser. No. 09/211,783, filed Dec. 15, 1998, now U.S. Pat. No. 6,383,204.

BACKGROUND OF THE INVENTION

1. Field of the Invention

This invention relates generally to implantable devices for interventional therapeutic treatment or vascular surgery, and more particularly concerns a variable stiffness vasoocclusive coil that exhibits variable stiffness along the length of the coil.

2. Description of Related Art

The art and science of interventional therapy and surgery has continually progressed towards treatment of internal defects and diseases by use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, treatment of vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein. That vasoocclusive device comprises one or more vasoocclusive members wound to form a generally spherical or ovoid shape in a relaxed state. The vasoocclusive members can be a helically wound coil or a co-woven braid formed of a biocompatible material, and the device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate, which can potentially be released during vascular surgery.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed.

One known technique for filling wide neck aneurysms involves breaking a coil or permanently deforming a coil within a vessel utilizing a balloon. However, substantial risks to a patient are involved in such a procedure, and a coil which has soft or deformable segments may offer less risk to a patient. As a coil is inserted into the aneurysm, the coil deforms and sets it shape, but over time a coil will typically assume its original shape, which is unlikely to correspond to the shape of the vessel being filled. Filling of a variety of types of aneurysms of various sizes and shapes may benefit by use of a variable stiffness coil that can deform more readily at certain predetermined sections. As such a variable stiffness coil is inserted into the aneurysm, the coil will deform to conform to the shape and size of the vessel being filled, and will set its shape, but unlike a helical coil which over time takes on its original shape, a variable stiffness, deformable coil will permanently deform in a random configuration, to thereby fill an aneurysm more evenly and completely over long periods of time.

A variable cross-section conical vasoocclusive coil is known that can achieve variations in stiffness of the coil by variation of the diameter in different regions of the coil or variations in the composition of the coil. Methods are also known for construction of a stent with a varying radial spring force, by heat treatments, by varying the stent frame thickness, selectively machining stent ring frames, using different alloys of the ring frames, and varying the Austenite finish transformation temperature (Af) of a shape memory alloy such as Nitinol. A guide wire is also known that is formed from one or more heat activated memory alloys, with intermediate portions that are selectively annealed to have variously curved shapes while the remainder of the wire remains straight when heated, and a stent is known that has U-shaped loop portions that are provided with greater flexibility by selective annealing to impart selective degrees of hardness to different portions.

It would be desirable to provide an vasoocclusive coil with primary and secondary shapes with variable stiffness along the length of the coil that can permanently deform in a random configuration that will permanently deform in a random configuration in order to fill an aneurysm more evenly and completely over long periods of time. The present invention meets these and other needs.

SUMMARY OF THE INVENTION

Briefly, and in general terms, the present invention provides for a variable stiffness vasoocclusive coil that exhibits variable stiffness along the length of the coil. Variable stiffness is accomplished by selectively heat treating certain segments of a primary or secondary coil. The primary coil can be selectively heat treated to form soft or deformable segments along the length of the coil, and can then be shaped into a secondary shape that is set by a heat treatment process. A secondary coil such as a three dimensional coil can be produced with variable stiffness through a selective heating of localized segments of the coil. Distal regions of the coil can also be heat treated to make the distal ends of the coil softer, more deformable, or less traumatic. Upon deployment, the coil will take on its pre-formed three dimensional shape, and will deform in a random three-dimensional shape to conform to the shape of the vessel or malformation into which the coil is introduced. The variable stiffness coil is advantageously formed of a shape memory metal, and variable stiffness can be achieved through aging of desired segments of the shape memory metal coil to raise the parent phase or Austenite phase finish temperature, thus making the treated segments of shape memory metal softer and more flexible.

The invention accordingly provides for an occlusive device for use in interventional therapy and vascular surgery adapted to be inserted into a portion of a vasculature for occluding the portion of the vasculature of a patient. The occlusive device comprises a variable stiffness coil formed from one or more flexible strands of a shape memory metal having a primary coil configuration, the coil having a plurality of segments heat treated to cause the plurality of segments to have reduced stiffness. In one presently preferred embodiment, the variable stiffness coil has an expanded secondary coil configuration with a secondary three dimensional shape, such as a spherical or helical shape. In a preferred aspect, the flexible strand comprises a superelastic material, which can be a shape memory metal such as a nickel titanium alloy. The shape memory nickel-titanium alloy is preferably heat treated such that the alloy is highly flexible at a temperature appropriate for introduction into the vasculature via a catheter, and after placement, the device will take on a shape designed to optimize the therapeutic purposes desired for the device.

The invention also provides for a method for making a variable stiffness occlusive coil for use in interventional therapy and vascular surgery adapted to be inserted into a portion of a vasculature for occluding the portion of the vasculature of a patient, comprising the steps of providing a coil formed from one or more flexible strands of a shape memory metal, the coil having a primary coil configuration and an initial stiffness; and heat treating a plurality of segments of the coil to cause the plurality of segments to have reduced stiffness. In one presently preferred embodiment, the step of providing a coil comprises heating the coil in a desired three dimensional configuration to set the three dimensional shape. In a preferred aspect of the method of the invention, the shape memory metal has an Austenite phase finish temperature, and the step of heating the coil comprises heating the coil at about 475° C. to 525° C. for about 1 to 20 minutes to set the Austenite phase finish temperature of the coil to about −5° C. to 10° C. The step of heat treating the coil can be accomplished by artificially aging a plurality of segments of the coil to raise the Austenite phase finish temperature to about 35° C. to 50° C., such as by heating a plurality of segments of the coil to a temperature of about 400° C. for a period of about 5 seconds to 30 minutes.

These and other aspects and advantages of the invention will become apparent from the following detailed description and the accompanying drawings, which illustrate by way of example the features of the invention.

DETAILED DESCRIPTION OF THE PREFERRED EMBODIMENTS

Modern techniques for filling wide neck aneurysms typically involve breaking a coil or permanently deforming a coil within a vessel utilizing a balloon, with attendant substantial risks to a patient, and a coil which has soft or deformable segments may offer less risk to a patient. While modern vasoocclusive coils deform and set their shape when they are introduced into a vessel, over time such coils will typically assume their original shape rather than to the shape of the vessel being filled. Filling of a variety of types of aneurysms of various sizes and shapes may benefit by use of a variable stiffness coil that can deform more readily at certain predetermined sections to fill an aneurysm more evenly and completely over long periods of time.

Figure 1:
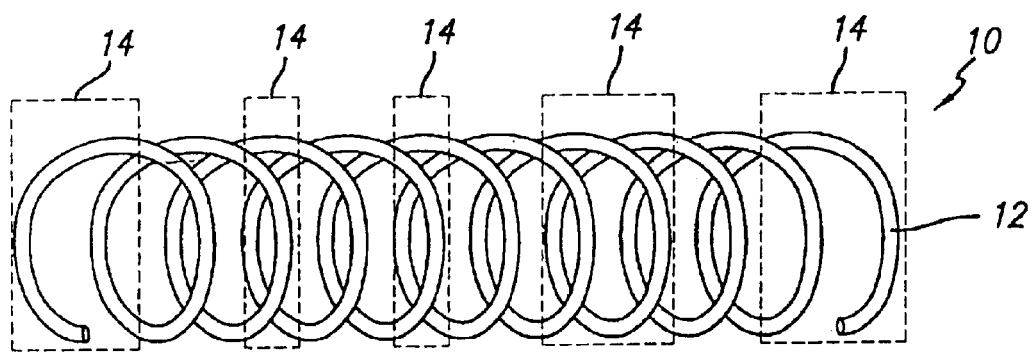
FIG. 1 is a primary helical vasoocclusive coil showing areas of heat treatment according to the invention.

As is illustrated in the drawings, the invention is embodied in an occlusive device for use in interventional therapy and vascular surgery adapted to be inserted into a portion of a vasculature for occluding a selected portion of the vasculature of a patient. In a presently preferred embodiment of the invention illustrated in FIG. 1, the occlusive device 10 is made from a strand of wire of approximately 0.001 inch to approximately 0.006 inch in diameter and comprises a coil 12 formed from one or more flexible strands of a superelastic, shape memory metal such as nickel-titanium alloy, for example. While the above stated range of diameters is presently known to be compatible with the invention, larger or smaller diameters may be useful for particular applications. The occlusive device typically has at least a primary coil configuration illustrated in FIG. 1, with a plurality of segments 14 being heat treated to cause the plurality of segments to have reduced stiffness.

Figure 2:
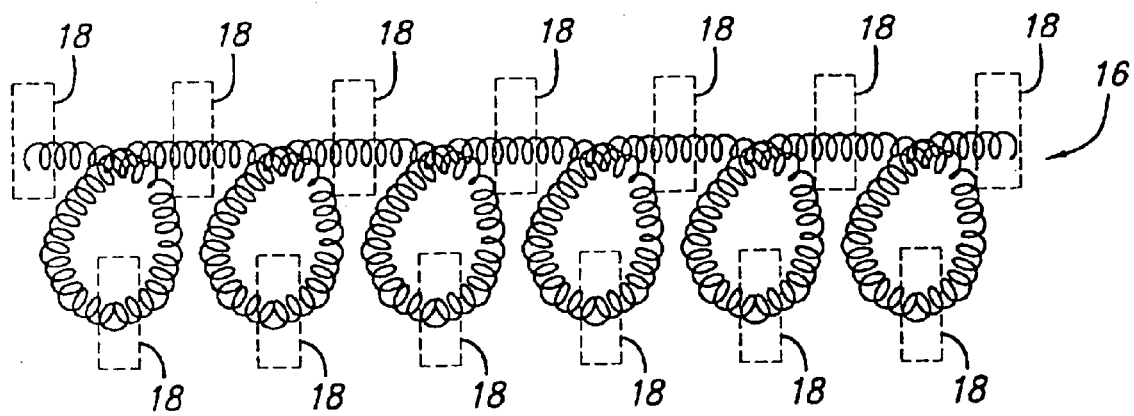
FIG. 2 is a secondary helical vasoocclusive structure formed using the primary helical coil of FIG. 1.
Figure 3:
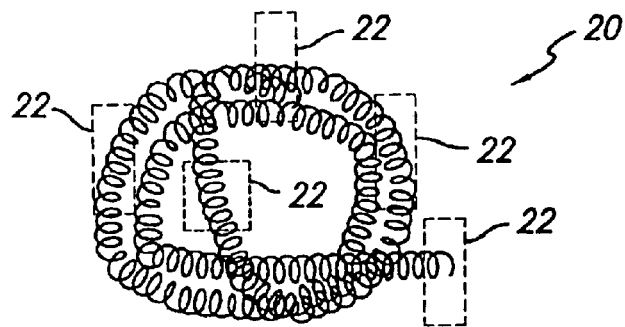
FIG. 3 is a secondary spherical vasoocclusive structure formed using the primary helical coil of FIG. 1.

In one presently preferred embodiment shown in FIG. 2, the variable stiffness coil has an expanded secondary coil configuration with a secondary helical three dimensional shape 16, with localized heat treated segments 18, although the variable stiffness coil can also have an expanded secondary coil configuration with a secondary spherical three dimensional shape 20, with localized heat treated segments 22, as illustrated in FIG. 3. The shape memory metal is preferably heat treated to be highly flexible at a temperature appropriate for introduction into the vasculature via a catheter, and such that after placement, the device will take on a shape designed to optimize the therapeutic purposes desired for the device.

Figure 4:
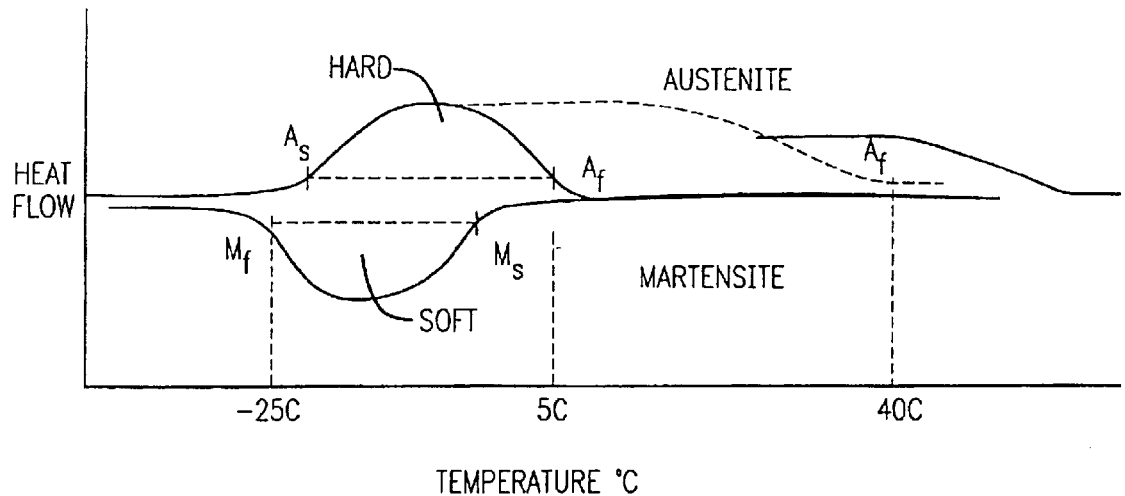
FIG. 4 is a graph illustrating the reduction in stiffness of a shape memory coil by heat treatment according to the principles of the invention.
Figure 5:
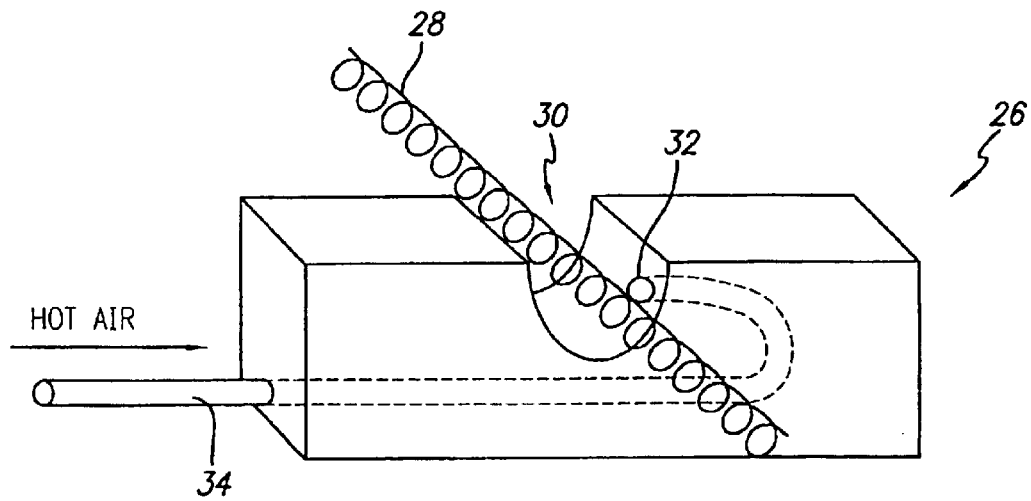
FIG. 5 is a schematic diagram of an apparatus for applying heat to segments of a vasoocclusive coil to form a variable stiffness vasoocclusive coil according to the invention.

The invention also provides for a method for making the variable stiffness occlusive coil. In a presently preferred embodiment, the variable stiffness occlusive coil can be formed from a coil 12 of one or more flexible strands of a superelastic shape memory metal. The coil preferably has at least a primary coil configuration and an initial stiffness, as is illustrated in FIG. 4, representing the change in stiffness of a heat treated segment of such a coil by application of heat to the segment, such as by the apparatus shown in FIG. 5. Variable stiffness of the heat treated segment can be achieved through artificial aging of the shape memory metal, such as Nitinol. The shape memory behavior of the shape memory metal can be modified by artificial aging of the material by heat treatment affecting the Austenitic transformation temperatures. When a shape memory alloy such as nickel titanium alloy is deformed, and then heated to recover its original parent or Austenite shape, the original shape corresponds to the shape of the alloy in the relatively high temperature range of the parent phase. Once the Austenite phase finish temperature (Af) is reached, the nickel titanium alloy becomes stiffened. However, artificial aging of the nickel titanium alloy can raise the Af temperature, thus making the material act softer at higher temperatures. The coil is preferably initially heated in a desired three dimensional configuration to set the three dimensional by heating the coil, such as in a salt pot, at about 475° C. to 525° C. for about 1 to 20 minutes to set the Austenite phase finish temperature of the coil to about −5° C. to 10° C. As is illustrated in FIG. 5, heat treating of a segment of the coil will cause the segment to have reduced stiffness, such as by artificially aging the segment of the coil to raise the Austenite phase finish temperature to about 35° C. to 50° C., by heating a plurality of segments of the coil to a temperature of about 400° C. for a period of about 5 seconds to 30 minutes. This can be accomplished by placing the primary or secondary shape coil in a heated air box 26 supplying hot air from a source of heated air (not shown). The air box, typically made of brass, for example, has a channel 30 in which the coil can be placed to expose the coil 28 to a flow of hot air from a port 32 that is typically 0.020 inches to 0.500 inches in diameter, conveyed to the port through a conduit 34 that extends through the air box. In this manner, localized heating can be provided to desired portions of the coil, at controlled temperatures for prescribed periods of time. Alternatively, heating of segments of the coil can be achieved by other means, such as by a laser, or by electrical heating, or other common types of heating elements.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for making a variable stiffness occlusive coil for use in interventional therapy and vascular surgery adapted to be inserted into a portion of a vasculature for occluding the portion of the vasculature of a patient, comprising the steps of:

providing a coil formed from at least one flexible strand of a flexible shape memory metal having an Austenite phase finish temperature, said coil having a primary coil configuration; and artificially aging a plurality of segments of said coil to cause said plurality of segments to have an Austenite phase finish temperature that is greater than the Austenite phase finish temperature of the remainder of the variable stiffness coil.

2. The method of claim 1, wherein said step of providing a coil comprising heating said coil in a desired three dimensional configuration to set said three dimensional configuration.

3. The method of claim 1, wherein said step of artificially aging said plurality of segments of said coil raises the Austenite phase finish temperature of said plurality of segments of said coil to about 35° C. to 50° C.

* * * * *